United States Patent
Arrizza

(10) Patent No.: US 10,305,992 B2
(45) Date of Patent: *May 28, 2019

(54) ASSOCIATING DIALYSIS ACCESSORIES USING WIRELESS COMMUNICATION

(71) Applicant: Fresenius Medical Care Holdings, Inc., Waltham, MA (US)

(72) Inventor: John Arrizza, San Diego, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/158,378

(22) Filed: Oct. 12, 2018

(65) Prior Publication Data

US 2019/0116226 A1    Apr. 18, 2019

Related U.S. Application Data

(63) Continuation of application No. 15/709,746, filed on Sep. 20, 2017, now Pat. No. 10,129,338, which is a
(Continued)

(51) Int. Cl.
*H04L 29/08* (2006.01)
*A61M 1/16* (2006.01)
(Continued)

(52) U.S. Cl.
CPC ............. *H04L 67/12* (2013.01); *A61M 1/14* (2013.01); *A61M 1/1603* (2014.02);
(Continued)

(58) Field of Classification Search
CPC ......... H04L 67/12; H04B 5/0031; H04B 5/02; G06F 19/00; H04W 4/80; A61M 1/1603;
(Continued)

(56) References Cited

U.S. PATENT DOCUMENTS 6,673,314 B1    1/2004    Burbank et al.
7,033,539 B2    4/2006    Krensky et al.
(Continued)

FOREIGN PATENT DOCUMENTS

DE    202012005295    9/2012
DE    102012020945    4/2014
(Continued)

OTHER PUBLICATIONS

Application Document, Bluetooth Secure Simple Pairing Using NFC, Bluetooth Special Interest Group, NFC Forum, NFCForum-AD-BTSSP-1.0, Oct. 18, 2011, 32 pages.
(Continued)

*Primary Examiner* — Eugene Yun
(74) *Attorney, Agent, or Firm* — Fish & Richardson P.C.

(57) ABSTRACT

A method comprising: establishing a wireless connection between a first medical device and a second medical device, comprising: receiving, by the first medical device, via a short-range wireless technology protocol, connection information related to the second medical device; and establishing, by the first medical device, a wireless connection with the second medical device based on the connection information.

18 Claims, 12 Drawing Sheets

Related U.S. Application Data continuation of application No. 14/640,364, filed on Mar. 6, 2015, now Pat. No. 9,800,663.

(51) Int. Cl.
| | | |
|---|---|---|
| *H04W 4/80* | (2018.01) | |
| *G16H 40/63* | (2018.01) | |
| *A61M 1/14* | (2006.01) | |
| *G06F 19/00* | (2018.01) | |
| *H04B 5/02* | (2006.01) | |
| *H04B 5/00* | (2006.01) | |

(52) U.S. Cl.
CPC ............. *G06F 19/00* (2013.01); *G16H 40/63* (2018.01); *H04B 5/0031* (2013.01); *H04B 5/02* (2013.01); *H04W 4/80* (2018.02); *A61M 2205/3569* (2013.01); *A61M 2205/3584* (2013.01)

(58) Field of Classification Search
CPC ............. A61M 1/14; A61M 2205/3569; A61M 2205/3584; G16H 40/63
USPC ........................................................ 455/41.1
See application file for complete search history.

(56) References Cited

U.S. PATENT DOCUMENTS

| | | | |
|---|---|---|---|
| 7,044,927 B2 | 5/2006 | Mueller et al. | |
| 7,699,806 B2 | 4/2010 | Ware et al. | |
| 8,190,651 B2 | 5/2012 | Treu et al. | |
| 8,313,642 B2 | 11/2012 | Yu et al. | |
| 8,315,885 B2 | 11/2012 | Krogh et al. | |
| 8,449,471 B2 | 5/2013 | Tran | |
| 8,549,600 B2 | 10/2013 | Shedrinsky | |
| 8,776,246 B2 | 7/2014 | Allegri et al. | |
| 8,871,095 B2 | 10/2014 | Yu et al. | |
| 8,905,959 B2 | 12/2014 | Basaglia | |
| 8,909,613 B2 | 12/2014 | Treu et al. | |
| 8,996,393 B2 | 3/2015 | Sobie | |
| 9,257,029 B1 | 2/2016 | Hendrick, III | |
| 9,314,207 B2 | 4/2016 | Marterstock | |
| 9,800,663 B2 * | 10/2017 | Arrizza | A61M 1/1603 |
| 9,913,940 B2 | 3/2018 | Court | |
| 2008/0010091 A1 | 1/2008 | Kim | |
| 2009/0275881 A1 | 11/2009 | Lo et al. | |
| 2010/0114639 A1 | 5/2010 | Leiendecker et al. | |
| 2011/0093294 A1 | 4/2011 | Elahi et al. | |
| 2012/0003933 A1 | 1/2012 | Baker et al. | |
| 2012/0100887 A1 | 4/2012 | Tekin | |
| 2012/0277546 A1 | 11/2012 | Soykan | |
| 2013/0138452 A1 | 5/2013 | Cork et al. | |
| 2013/0141329 A1 | 6/2013 | Halbert et al. | |
| 2013/0142367 A1 | 6/2013 | Berry | |
| 2013/0151274 A1 | 6/2013 | Bage | |
| 2013/0310726 A1 | 11/2013 | Miller et al. | |
| 2013/0346102 A1 | 12/2013 | Yu et al. | |
| 2014/0006510 A1 | 1/2014 | Hamilton et al. | |
| 2014/0121845 A1 | 5/2014 | Mueller | |
| 2014/0133530 A1 | 5/2014 | Maguire | |
| 2014/0276375 A1 | 9/2014 | Minkus | |
| 2014/0288947 A1 | 9/2014 | Simpson et al. | |
| 2015/0011970 A1 | 1/2015 | Kamen et al. | |
| 2015/0095041 A1 | 4/2015 | Kim | |
| 2016/0142894 A1 | 5/2016 | Papakonstantinou | |
| 2016/0212552 A1 | 7/2016 | Schneider | |

FOREIGN PATENT DOCUMENTS

| | | |
|---|---|---|
| EP | 2145451 | 12/2012 |
| JP | 2012-527308 | 11/2012 |
| JP | 2014-198244 | 10/2014 |
| WO | WO 2011/028261 | 12/2011 |
| WO | WO 2014/004448 | 1/2014 |
| WO | WO 2014/05034 | 5/2014 |
| WO | WO 2014/063798 | 5/2014 |
| WO | WO 2014/100687 | 6/2014 |

OTHER PUBLICATIONS

Jung et al, "Interoperability between Medical Devices using Near Field Communication", IEEE, Jun. 24, 2013, pp. 1-4.

International Search Report and Written Opinion in International Application No. PCT/US2016/019331, dated May 31, 2016, 13 pages.

International Preliminary Report on Patentability in International Application No. PCT/US2016/019331, dated Sep. 12, 2017, 8 pages.

* cited by examiner

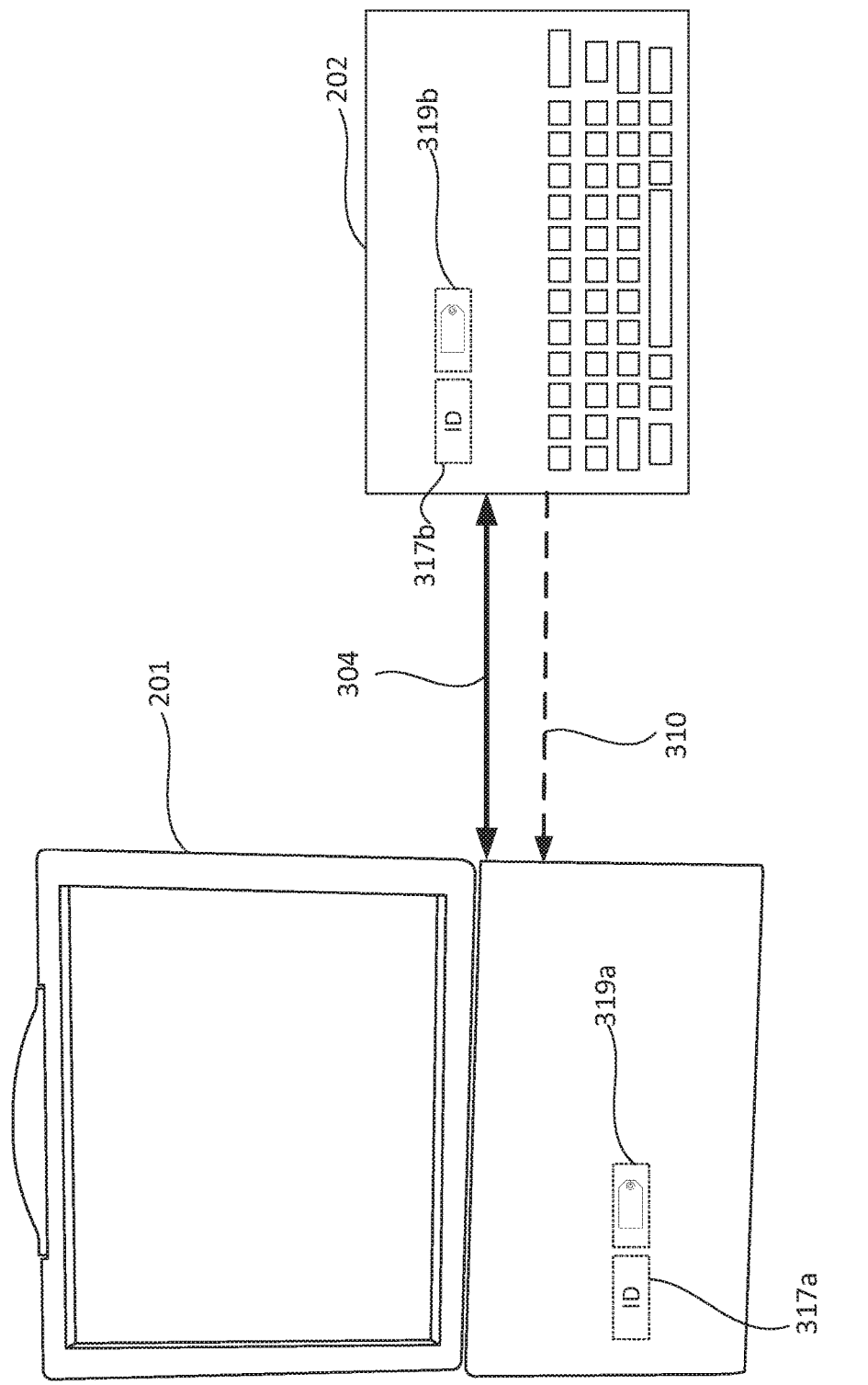

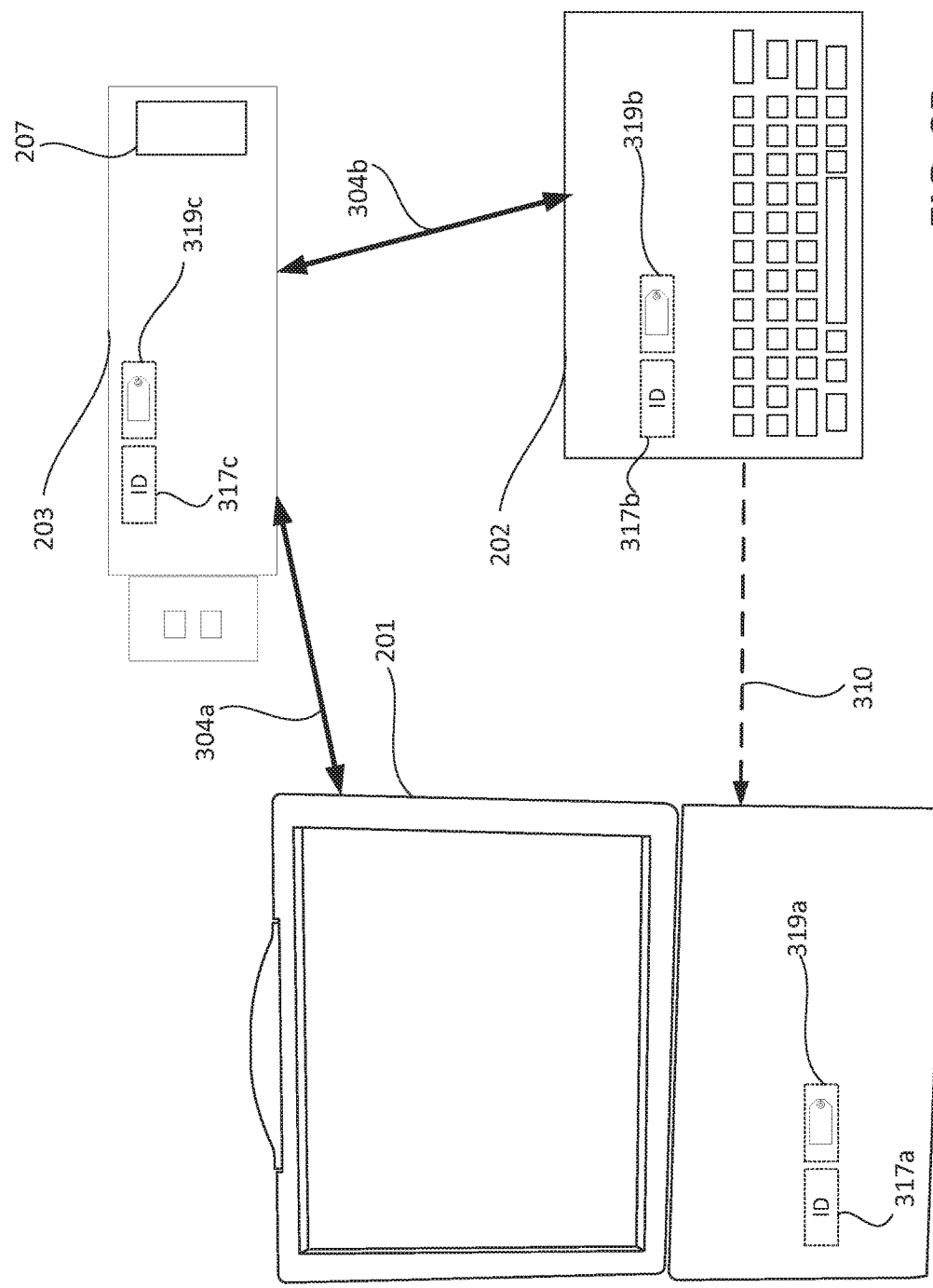

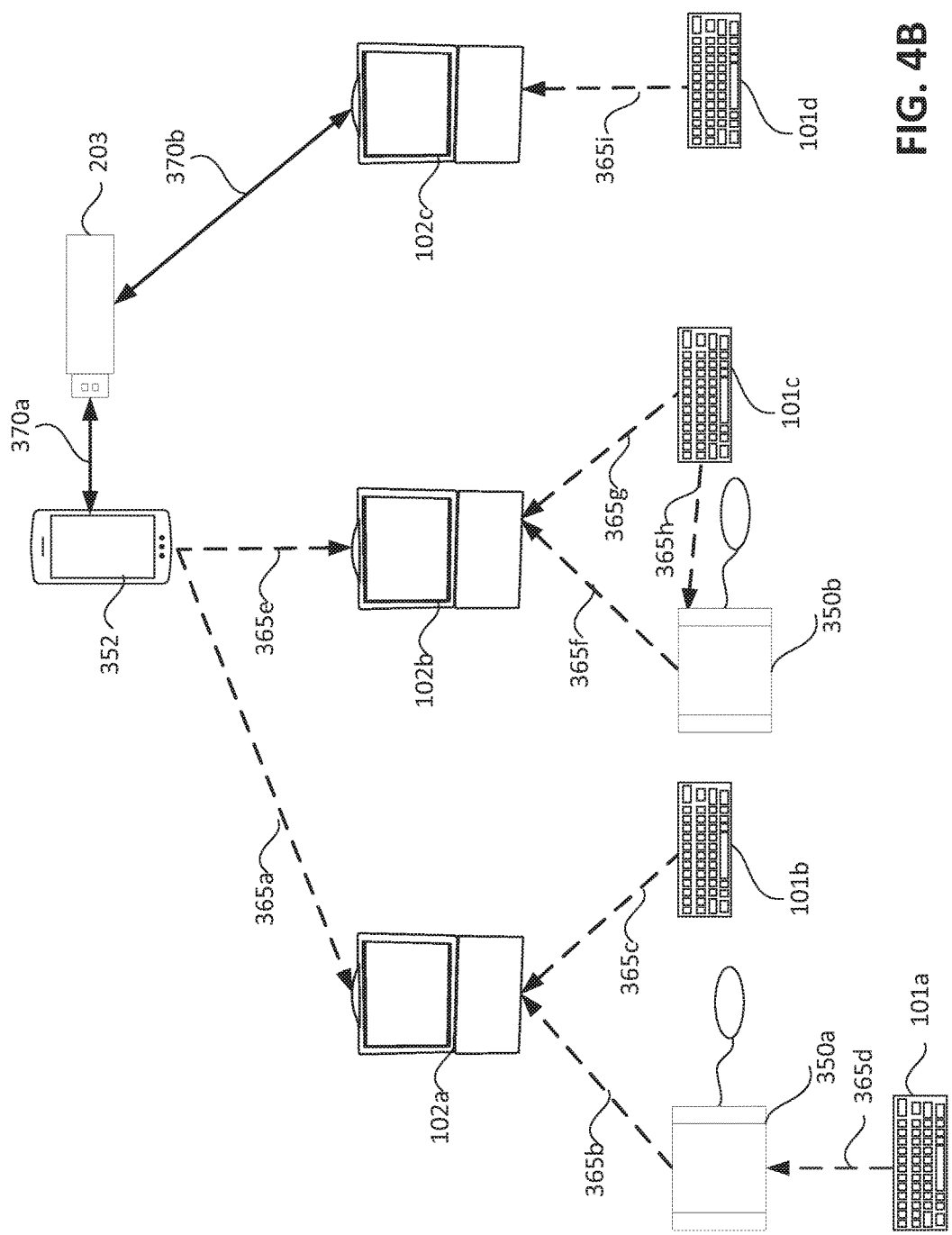

ASSOCIATING DIALYSIS ACCESSORIES USING WIRELESS COMMUNICATION

CROSS-REFERENCE TO RELATED APPLICATION

This application is a continuation and claims priority to U.S. Ser. No. 15/709,746, filed on Sep. 20, 2017, which is a continuation of U.S. Ser. No. 14/640,364, filed Mar. 6, 2015, now U.S. Pat. No. 9,800,663. The entire contents of each application is incorporated by reference herein.

TECHNICAL FIELD

This invention relates to wireless communication for dialysis systems.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then typically discarded.

The dialysis solutions or dialysates used during hemodialysis typically contain sodium chloride and other electrolytes, such as calcium chloride or potassium chloride, a buffer substance, such as bicarbonate or acetate, and acid to establish a physiological pH, plus optionally, glucose or another osmotic agent.

SUMMARY

In one aspect, a method includes establishing a wireless connection between a first medical device and a second medical device. Establishing the wireless connection includes receiving, by the first medical device, via a short-range wireless technology protocol, connection information related to the second medical device. Establishing the wireless connection also includes establishing, by the first medical device, a wireless connection with the second medical device based on the connection information.

Implementations can include one or more of the following features.

In some implementations, the wireless connection is established using a communication protocol other than the short-range wireless technology protocol. The connection information specifies information used by the communication protocol other than the short-range wireless technology protocol.

In some implementations, the method also includes receiving, by a connection device, from the second medical device, via the short-range wireless technology protocol, the connection information related to the second medical device. The method also includes providing, by the connection device, to the first medical device, via the short-range wireless technology protocol, the connection information related to the second medical device.

In some implementations, the connection device is a wand.

In some implementations, the connection device is a smartphone.

In some implementations, the method also includes receiving, by the second medical device, via the short range wireless technology protocol, connection information related to the first medical device.

In some implementations, the method also includes sending, from the first medical device, a request to establish a wireless connection with the second medical device.

In some implementations, the first medical device and the second medical device are positioned at a sufficient distance relative to each other for the first medical device and the second medical device to be close enough to communicate via the short-range wireless technology protocol.

In some implementations, the first medical device receives the connection information from the second medical device as a result of the first medical device and the second medical device making physical contact with each other.

In some implementations, at least one of the first and second medical devices includes an accelerometer configured to detect the physical contact.

In some implementations, the short-range wireless technology protocol is a Near Field Communication (NFC) protocol. The first medical device and the second medical device each includes a component configured to communicate via NFC.

In some implementations, the component includes an inductor.

In some implementations, the connection information related to the second medical device includes a wireless identifier.

In some implementations, the wireless identifier is unique to the device.

In some implementations, the first medical device is electrically isolated from the second medical device.

In some implementations, the first medical device comprises a dialysis machine.

In some implementations, the second medical device comprises an accessory configured to interact with a dialysis machine.

In some implementations, the second medical device comprises a blood pressure cuff.

In some implementations, the wireless connection comprises a Bluetooth connection.

In another aspect, a method includes establishing a wireless connection between a dialysis machine and a dialysis machine accessory. Establishing the wireless connection includes receiving, by the dialysis machine, a wireless identifier associated with the dialysis machine accessory. The wireless identifier is communicated by a connection device according to a first wireless communication protocol. The wireless identifier is associated with a second wireless communication protocol other than the first wireless communication protocol. Establishing the wireless connection also includes, using the wireless identifier associated with the dialysis machine accessory, establishing, by the dialysis machine and the dialysis machine accessory, a wireless connection using the second wireless communication protocol. The method also includes communicating medical data between the dialysis machine and the dialysis machine accessory using the second wireless communication protocol.

In another aspect, a system includes a medical device. The medical device includes a short-range wireless technology protocol antenna configured to receive a wireless identifier related to a medical device accessory via the short-range wireless technology protocol. The medical device also includes an antenna configured to establish a wireless connection with the medical device accessory via a communication protocol other than the short-range wireless technology protocol using the wireless identifier related to the medical device accessory.

Implementations can include one or more of the following advantages.

In some implementations, the methods described can allow a user to easily pair dialysis machine accessories with dialysis machines. Clinics that offer dialysis treatment typically have several dialysis machines, each of which has several dialysis machine accessories. The devices—both machines and accessories—can be connected to a wireless network such that the accessories can wirelessly communicate with the machines. For an accessory to communicate with a specific machine, the accessory can be virtually associated with the machine using the wireless network. The physical motion of tapping an accessory against a dialysis machine to virtually associate the accessory and the dialysis machine can ensure that the operator can easily select the physical identities of associated devices in a physical, visual, and tactile way. The methods also improve the efficiency of making virtual associations by reducing the need to manually enter connection information into dialysis machines and accessories. Connection information can be easily transmitted using the tapping motion described above. The methods described herein can further electrically isolate devices from one another by eliminating the need for communicating electrically sensitive data through electrical lines.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A is a schematic diagram of a wireless connection between a host device and an accessory device.

FIG. 3B is a schematic diagram of the wireless connection of FIG. 3A established by a connection device.

FIG. 4B is a block diagram depicting connections within the network shown in FIG. 4A.

Like reference symbols in the various drawings indicate like elements.

DETAILED DESCRIPTION

Figure 1:
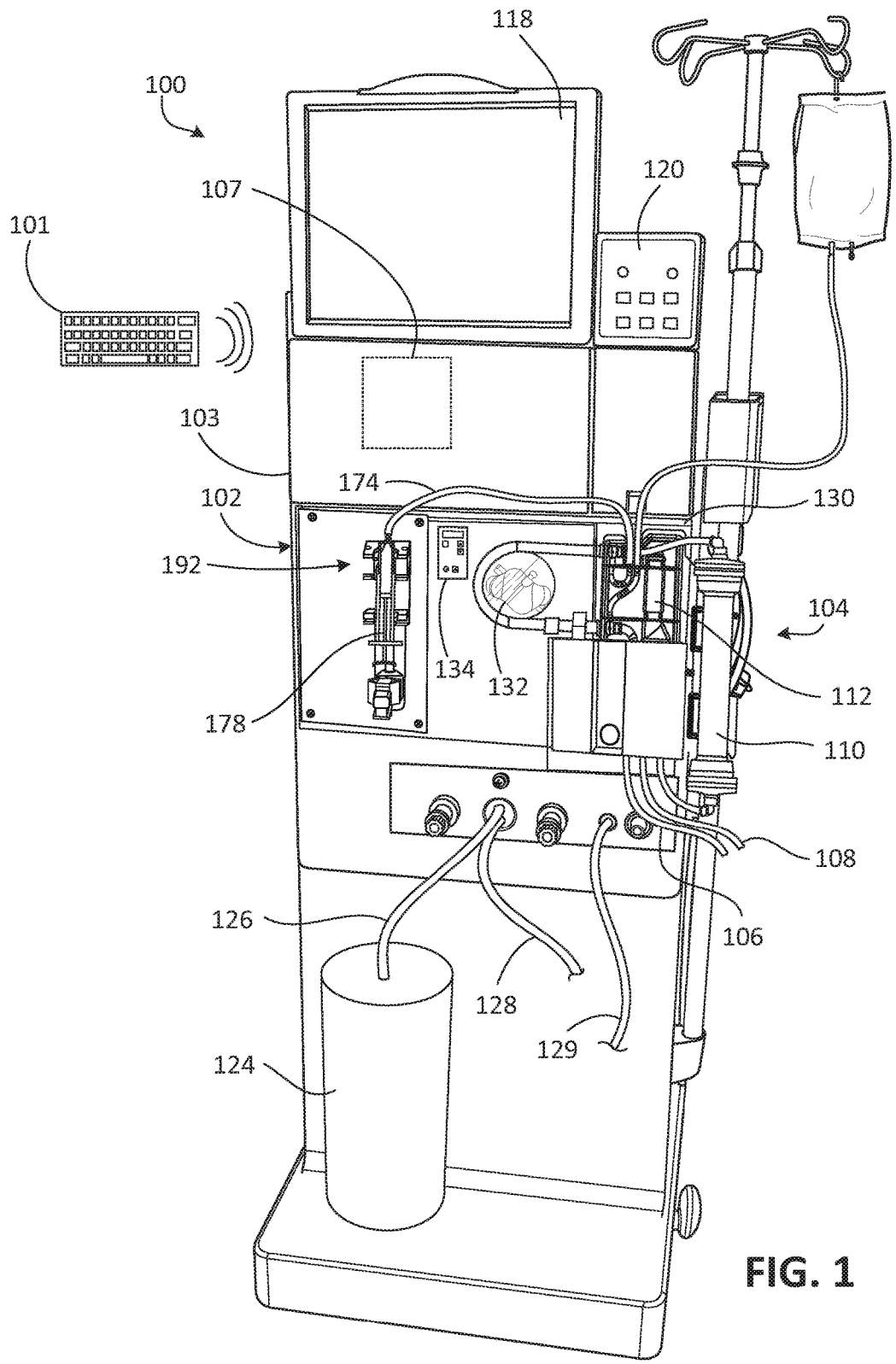
FIG. 1 is a front perspective view of a hemodialysis system.

Medical devices (e.g., dialysis machines, dialysis machine components, dialysis machine accessories, etc.) can be configured to wirelessly communicate with other medical devices through a connection between the devices. A "connection" established between devices as described herein refers to electronic communication between two or more devices such that data can be communicated between the devices. The connection can be a unidirectional or a bidirectional connection that allows data to move between two nodes in a network. A "node" herein is a member of a network connection (e.g., a virtual connection) and represents a corresponding physical device, such as the devices described above. Basic connections between devices allows the connected devices to determine the identity of other devices. A connection between devices can have a greater number of granted permissions than the basic connection described above. Such a connection is herein referred to as an "association." For example, in an association between devices, a first device can grant the second device input permissions such that the second device can serve as an input for the first device. In some systems, an operator can manually establish the wireless association by manually inputting connection information (e.g., a unique wireless identifier) into one or both of the device. However, inputting connection information, which generally includes a lengthy and unintuitive sequence of numbers, can be confusing or cumbersome for some operators.

In some examples, two or more medical devices that are part of a wireless network, such as a WiFi network, can share connection information with each other using a short-range wireless technology protocol, such as Near Field Communication (NFC) or Bluetooth. For example, two medical devices that each includes an NFC transceiver (alternatively, e.g., a Bluetooth transceiver) and a wireless transceiver can communicate with each other using the transceivers. The medical devices are equipped with sensor systems and controllers that can determine when the operator has performed an action with the medical devices that represents an intent to establish a wireless connection between the medical devices. In some implementations, the medical devices can be tapped together and/or positioned at a close distance relative to each other such that the NFC transceivers are within operable range of one another. The medical devices can then share their unique wireless identifiers with one another through the NFC protocol. Once one of the medical devices knows the connection information of the other medical device, a wireless association can be established between the two medical devices.

In some examples, the medical devices require high voltage power cables that connect the devices to a central power source. These power cables can be shielded such that their voltages do not interfere with one another. However, as physical data lines utilize low voltages, the power cables can still interfere with the signals carried by the physical data lines. In some examples, the medical devices can communicate information between one another. Physical data lines can be conventionally used, but the fidelity of communication signals in the physical data lines can be easily compromised by, for example, the high voltages of the power cables. Thus, medical devices using physical data lines may not be electrically isolated from one another. The wireless communication methods described herein eliminate the need for conventional physical data connections, and thus electrically isolate the devices from one another.

In some examples, a connection device that includes an NFC transceiver can be used to share connection information of various medical devices with other medical devices. For example, the connection device can be tapped against and/or positioned at a sufficient distance from a first medical device such that the NFC transceiver of the connection device can communicate with the NFC transceiver of the first medical device. The connection device can receive the unique wireless identifier of the first medical device using the NFC protocol. The connection device can then be tapped against and/or positioned at a sufficient distance from a second medical device such that the NFC transceiver of the connection device can provide the unique wireless identifier of the first medical device to the second medical device. Using the wireless identifiers, the medical devices can then establish a wireless connection with each other. In some implementations, the connection device can receive the unique wireless identifier from each device and directly communicate the wireless identifiers to the wireless network. The wireless network can then cause a connection to be established between the first and second medical devices. In some examples, the connection device is a wand or a smartphone.

FIG. 1 shows a hemodialysis system 100 configured to wirelessly communicate with other medical devices. The hemodialysis system 100 includes a hemodialysis machine 102 connected to a disposable blood component set 104 that partially forms a blood circuit. The operator can manage and control treatment parameters of the hemodialysis system 100 using an external wireless keyboard 101. During hemodialysis treatment, an operator connects arterial and venous patient lines 106, 108 of the blood component set 104 to a patient. The blood component set 104 includes an air release device 112, which contains a self-sealing vent assembly that allows air but does not allow liquid to pass. As a result, if blood passing through the blood circuit during treatment contains air, the air release device 112 will vent the air to atmosphere.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130.

The operator uses a blood pump module 134 to operate the blood pump 132. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

The hemodialysis machine 102 further includes a dialysate circuit formed by the dialyzer 110 various other dialysate components and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

A dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As will be described below, as the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a user interface with input devices such as a touch screen 118 and a control panel 120. The touch screen 118 and the control panel 120 allow the operator to input various different treatment parameters to the hemodialysis machine 102 and to otherwise control the hemodialysis machine 102. The touch screen 118 displays information to the operator of the hemodialysis system 100. The touch screen 118 can also indicate whether a peripheral or accessory device, such as the keyboard 101, is connected to the hemodialysis machine 102. The keyboard 101 is a wireless keyboard that connects to the hemodialysis machine 102 by communicating directly or indirectly with a communication system 107 in the dialysis machine 102. During treatment, the keyboard 101 and other peripheral devices can be used to control, monitor, and determine treatment parameters and variables.

Figure 2A:
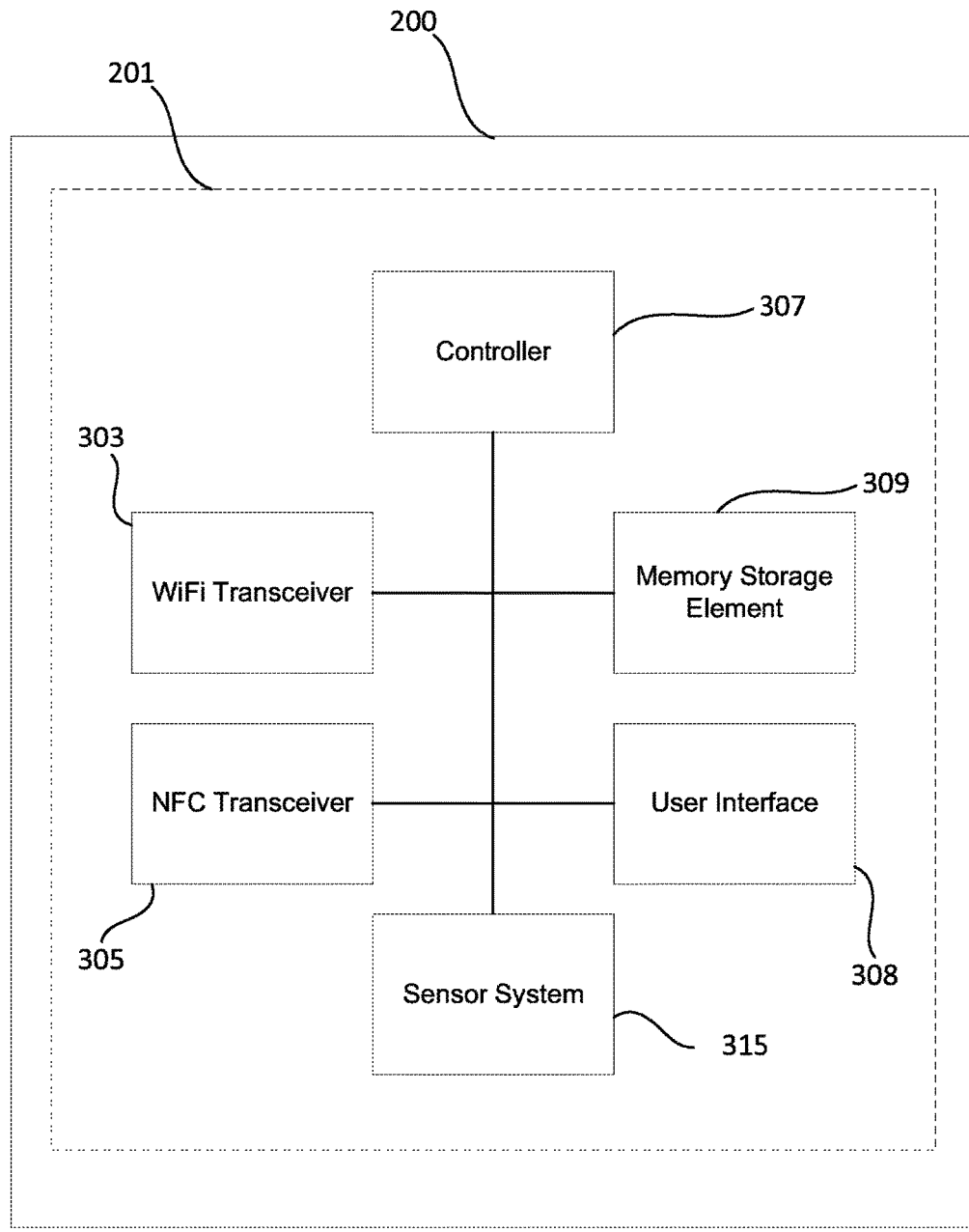
FIG. 2A is a schematic diagram of a communications system of a device used to establish a wireless connection.

FIG. 2A is a block diagram of a communications system 201 of a device 200 that can be used to establish a wireless association between two devices. The device 200 can itself be one of the devices connected by the wireless association. The wireless association can be formed using a wireless protocol such as, for example, WPA, WPA2, or WEP, among others. Alternatively, the device can facilitate the establishment of the wireless association between two other devices. The device 200 can be a host device (e.g., the hemodialysis machine 102), a peripheral device (e.g., the wireless keyboard 101 of FIG. 1), or a connection device (the function of which is described in more detail below).

A controller 307 of the device 200 accesses and controls the communications system 201, which includes a wireless transceiver 303, an NFC transceiver 305, a user interface 308, and a memory storage element 309. The wireless transceiver 303 is an antenna that connects the device 200 to a wireless network (not shown) to transmit and receive data using wireless connections. The NFC transceiver 305 of the device 200 is an antenna that transmits and receives data using NFC connections. In some examples, the antenna forms or includes an inductor such that when two NFC transceivers are placed within range of one another, they form a transformer that generates an electromagnetic force inversely proportional to the distance between the transceivers. The controller 307 manages transmission and receipt of data in the communications system 201 and also stores data received from the wireless transceiver and/or the NFC transceiver 305 on the memory storage elements 309. The controller 307 further retrieves data from the memory storage element 309 to transmit using the wireless transceiver 303 and/or the NFC transceiver 305. The controller 307 executes subroutines (which will be described in more detail below) stored on the memory storage element 309. The user interface 308 displays communications-related information and/or allows the operator to input data. For example, the user interface 308 can show the devices with which the device 200 has wireless associations and/or devices that have granted input permissions to the device 200. The operator can further use the user interface 308 to accept connection requests or to set default settings for the subroutines 330, which will be described below. In this example, the device 200 includes a sensor system 315. The sensor system 315 on the device 200 includes, for example, accelerometers for collecting information related to a motion of the device.

Figure 2B:
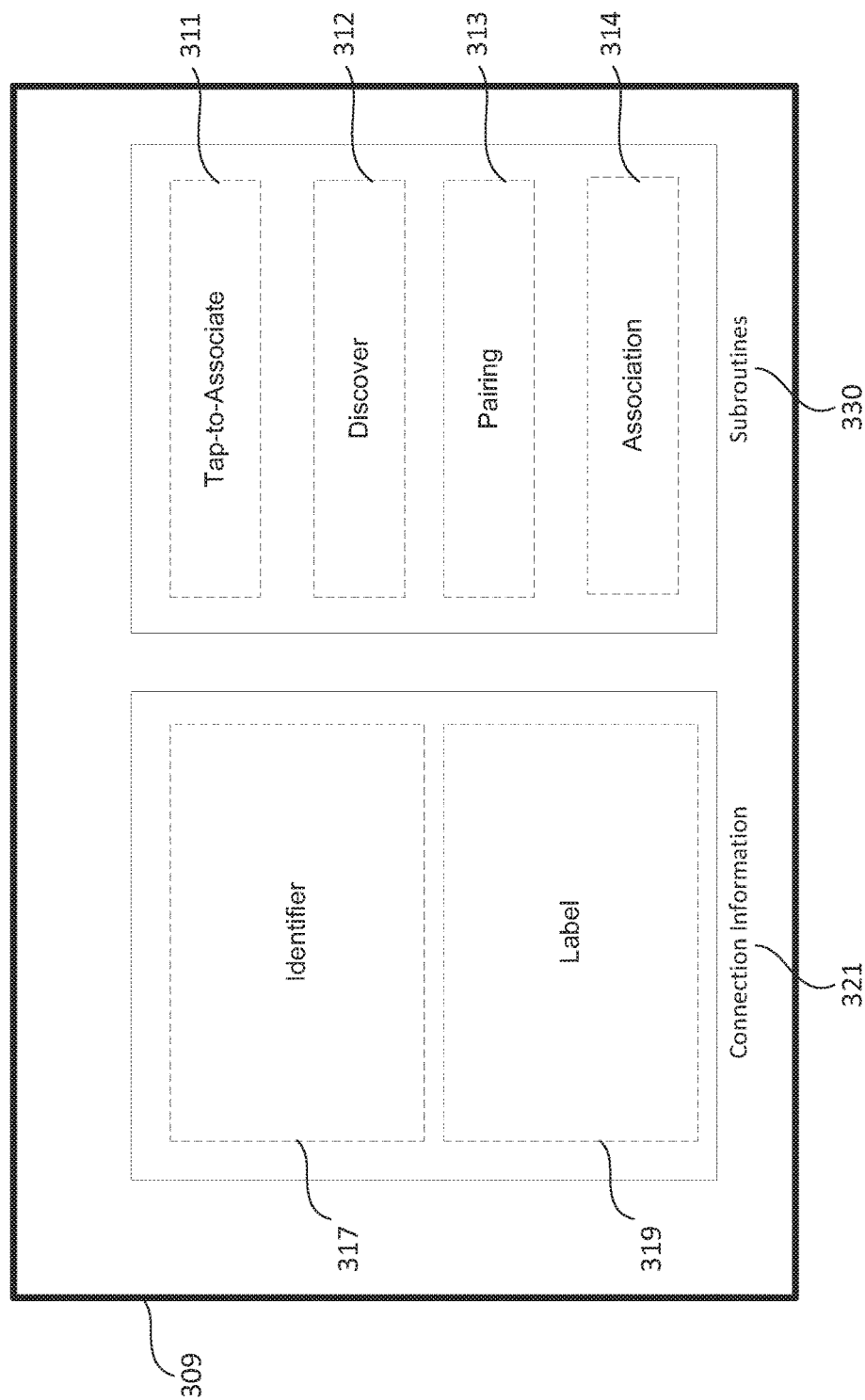
FIG. 2B is a schematic diagram of data contained on a memory storage element of the communications system of FIG. 2A.

FIG. 2B schematically shows examples of data stored on an example memory storage element 309 of the device 200. The memory storage element 309 can store connection information 321 that classifies the device 200 and uniquely identifies the device 200. The connection information 321 includes an identifier 317 and a label 319. The identifier 317 represents the unique identity of the device on the wireless network, such as, for example, a WiFi network. The label 319 determines the type or class of the device. The label can be HOST, PERIPHERAL, or CONNECTOR. As will be described below, the identifier 317 can be used to determine the devices connected using the wireless protocol, and the labels can be used to determine characteristics of the connection.

The memory storage element 309 further contains subroutines 330 that can be executed by the controller 307 to establish a wireless association (e.g., the wireless association 310 of FIG. 3A-B, which will be described below). These subroutines 330 include a Tap-to-Associate Subroutine 311, Discover Subroutine 312, a Pairing Subroutine 313, and an Association Subroutine 314.

The Tap-to-Associate Subroutine 311 allows a user to pair and associate devices by tapping the device 200 against a second device that is also executing a Tap-to-Associate Subroutine 311. The default settings of the device 200 are set such that the Tap-to-Associate Subroutine 311 is automatically executing by default. In this example, when the controller 307 is executing the Tap-to-Associate Subroutine 311, the controller 307 can receive information related to a motion of the device from the sensor system 315. The Tap-to-Associate Subroutine 311 can cause the controller 307 to continuously receive the motion information until the motion exceeds a threshold value. When the motion exceeds the threshold value, the Tap-to-Associate Subroutine 311 can sequentially execute the Discover Subroutine 312 and the Pairing Subroutine 313.

The Discover Subroutine 312 enables functions of the NFC transceiver 305 so that the device 200 can communicate with other devices having enabled NFC transceivers. In particular, the controller 307 executes the Discover Subroutine 312 to place the NFC transceiver 305 in a virtually discoverable state such that other nearby NFC transceivers can detect (or discover) the NFC transceiver 305 of the device 200. (A device with an NFC transceiver in a discoverable state is hereby also called a "discoverable device.") The NFC transceiver 305 of the discoverable device 200 can listen for other discoverable devices by creating, for example, an NFC server socket. The Discover Routine 312 is initialized after the Tap-to-Associate Subroutine 311 is triggered, as described above.

The Pairing Subroutine 313 can connect two devices using the NFC transceivers so that the devices can share connection information with one another. In particular, after the Discover Subroutine 312 and the NFC transceiver 305 has discovered a second device, the controller can execute the Pairing Subroutine 313 to use the NFC transceiver 305 to pair with the second device. The second device selected by the Pairing Subroutine 313 is, for example, a discoverable device in closest proximity to the device 200. Upon initiating a pairing with the second device, the NFC server socket can return an NFC socket for the second device, thus forming an NFC connection to pair the device 200 with the second device. Using the NFC connection, the device 200 retrieves and stores the identifier and the label of the second device. The Pairing Subroutine also causes the device 200 to send its own identifier 317 and label 319 to the second device using the NFC connection.

The Association Subroutine 314 forms the wireless association and determines the characteristics of the wireless association. After completing the Pairing Subroutine 313, the device 200 initiates the Association Subroutine 314. The Association Subroutine uses the identifiers 317 and labels 319 for the two devices to form the wireless association between the two devices. The identifiers determine the two nodes that the wireless association connects, and the labels determine the type of wireless association between the nodes. The identifier retrieved from the Pairing Subroutine 313 is used to determine one of two nodes.

The identifier that the Association Subroutine 314 uses to determine the second node depends on the label 319 of the device 200. If the device 200 has a HOST or PERIPHERAL label, the Association Subroutine 314 uses the device's own identifier 317 to define the second node. The type of wireless association formed then depends on the label of the second device and the label of the device 200. An example of such an implementation will be described below with respect to FIG. 3A.

If the device 200 has a CONNECTOR label, the device 200 does not use its own identifier 317 as the second node. Instead, the operator pairs the device 200 (e.g., via the Tap-to-Associate Subroutine 311) with a third device to retrieve an identifier for the second node. The label of the second device and the label of the third device determine the type of wireless association formed between the two devices. An example of such an implementation will be described below with respect to FIG. 3B.

As a result of the two conditions described above for the inputs of the Association Subroutine, the Association Subroutine 314 forms wireless associations between devices with PERIPHERAL or HOST labels. In addition, one of the devices can be the device 200. When one device is a PERIPHERAL device and the other device is a HOST device, the two devices form an association such that, for example, the HOST device grants permission to the PERIPHERAL device to serve as an input device for the HOST device. The PERIPHERAL device thus can control functions of the HOST device and/or can deliver data to the HOST device. When two PERIPHERAL devices or two HOST devices are connected using the Association Subroutine 314, the Association Subroutine 314 may prompt the operator to indicate which device serves as an input device and which device serves as an input receiving device.

Methods of Use

FIGS. 3A-B depict an example of a wireless association 310 established between a host device 201 and a peripheral device 202. In this example, the host device 201 is a hemodialysis machine, and the peripheral device 202 is a keyboard. Referring to FIG. 3A, the host device 201 and the peripheral device 202 are paired directly to form the wireless association 310. Referring to FIG. 3B, the connection device 203 helps to establish the wireless association 310 between the host device 201 and the peripheral device 202. The wireless association 310 can allow the peripheral device 202 to controls treatment parameters through data inputted through the peripheral device 202. The operator can modify treatment parameters set on the host device 201 by entering treatment instructions into the peripheral device 202 which are sent to the host device 201 through the wireless association 310.

The wireless association can be established using the following methods: (i) the host device 201 and the peripheral device 202 directly pair with one another to form the wireless association (as shown in FIG. 3A), or (ii) a connection device 203 communicates with each of the host device 201 and the peripheral device 202 and then causes the wireless association 310 to be established between the host device 201 and the peripheral device 202 (as shown in FIG. 3B). Both of these methods will be described in detail below. The devices 201, 202, 203 include the communications systems as described with respect to FIGS. 2A-B. Referring to FIG. 3A, the host device 201 having a HOST label 319a and a unique identifier 317a and the peripheral device 202 having a PERIPHERAL label 319b and a unique identifier 317b are paired directly to form the wireless association 310. In FIG. 3B, the connection device 203 having CONNEC-TOR label 319c and a unique identifier 317c helps to establish the wireless association 310 between the host device 201 and the peripheral device 202. The connection device 203 can be a wand that includes the aspects as described above for the connection device.

FIG. 3A shows an example of associating the host device 201 with the peripheral device 202 to form the wireless association 310. The operator directly pairs the host device 201 with the peripheral device 202 using an NFC connection 304.

The operator brings the peripheral device 202 within a close proximity of the host device 201 (e.g., within the NFC range of the NFC transceiver of the host device 201). In some implementations, the peripheral device 202 can be tapped against the host device 201. The tapping gesture can generate a particular motion signature of the peripheral device 202 that triggers the Tap-to-Associate Subroutine 311 of the peripheral device 202. The tapping gesture can also generate a particular motion signature of the host device 201 that can trigger the Tap-to-Associate Subroutine 311 of the host device 201. As a result, the host device 201 and peripheral device 202 can initiate their respective Discover Subroutines 312 and can be placed in discoverable states.

The Pairing Subroutine 313 can then be initiated, causing the peripheral device 202 to pair with a device with a discoverable NFC transceiver. In some implementations, such as when there are multiple devices in discoverable states, the peripheral device 202 may pair with the device that is in closest proximity to the peripheral device 202. The devices 201, 202 are typically physically close to one another when the operator taps the peripheral device 202 against the host device 201. As a result, the peripheral device 202 can pair with the host device 201.

Once the NFC connection 304 is established, the peripheral device 202 can then retrieve the HOST label 319a and the identifier 317a of the host device 201 through the NFC connection 304. The peripheral device 202 can also send the PERIPHERAL label 319b and the identifier 317b of the peripheral device 202 to the host device 201 using the NFC connection 304.

After the Pairing Subroutine is complete, the peripheral device 202 can then initiate the Association Subroutine 314 to determine the type of wireless association formed and the nodes connected by the wireless association. In some implementations, the Association Subroutine 314 identifies the identifier 317a stored on the peripheral device 202 as the first of two nodes of the wireless association. The Association Subroutine 314 can further identify the identifier 317b—the identifier of the peripheral device 202—as the second node of the wireless association. The identifier 317b is associated with the PERIPHERAL label 319b, and the identifier 317a is associated with the HOST label 319a. As a result, the Association Subroutine 314 can set the peripheral device 202 to be an input device for the host device 201. In other words, the Association Subroutine 314 can instruct the host device 201 to grant input permissions to the peripheral device 202, thus forming the wireless association 310.

FIG. 3B shows an example of associating the host device 201 with the peripheral device 202 to form the wireless association 310 using the connection device 203. The connection device 203 can be used to establish a wireless association between two devices. Generally, the connection device 203 can establish a wireless association between a device with a HOST label (e.g., the host device 201) and a device with a PERIPHERAL label (e.g., the peripheral device 202). The connection device 203 includes a control screen 207 (e.g., the user interface of FIG. 2A) that the operator uses to manage the connections of the connection device 203 (e.g., NFC, USB, or WiFi connections) and subsequent wireless associations established by the connection device 203 (e.g., the wireless association 310).

By way of general overview, in the example described below with respect to FIG. 3B, the operator first pairs the host device 201 with the connection device 203 to form the NFC connection 304a. The operator then pairs the peripheral device 202 with the connector device 203 to form the NFC connection 304b. Labels 317a, 317b and identifiers 319a, 317b, which are transferred and stored through the two pairings, allow the connection device 203 to cause the wireless association 310 to be formed between the host device 201 and the peripheral device 202. Details of each of these steps will be described in detail below. The wireless association 310 can be formed by, for example, a central server of the wireless network or by the connection device 203.

The operator can form the NFC connection 304a by bringing the connection device 203 within a close proximity of the host device 201 (e.g., within the NFC range of the NFC transceiver of the host device 201) and tapping the connection device 203 against the host device 201. The tapping motion can trigger the Tap-to-Associate Subroutines of the connection device 203 and the host device 201 and can place them in discoverable states. The Tap-to-Associate Subroutine can further cause the connection device 203 to initialize the Pairing Subroutine, which can instruct the connection device 203 to pair with the physically closest device with a discoverable NFC transceiver. As the operator tapped the connection device 203 against the host device 201 to run the Tap-to-Associate Subroutine, the devices 201, 203 are physically closest to one another as well. As a result, the connection device 203 can pair with the host device 201. As a result, the NFC connection 304a pairs the connection device 203 and the host device 201. The connection device 203 then can retrieve the HOST label 319a and the identifier 317a of the host device 201 using the NFC connection 304a. The connection device 203 also can send the CONNECTOR label 319c and the identifier 317c to the host device 201 using the NFC connection 304a.

After the Pairing Subroutine is complete, the connection device 203 can initiate the Association Subroutine 314. As the label 319c of the connection device 303 is CONNECTOR, the Association Subroutine 314 can instruct the operator to pair the connection device to another device to complete the wireless association.

The operator can form the NFC connection 304a by bringing the connection device 203 within a close proximity of the peripheral device 202 (e.g., within the NFC range of the NFC transceiver of the peripheral device 202) and tapping the connection device 203 against the peripheral device 202. The tapping motion can trigger the Tap-to-Associate Subroutines of the connection device 203 and the peripheral device 202 and places them in discoverable states. The Tap-to-Associate Subroutine further can cause the connection device 203 to initialize the Pairing Subroutine, which can instruct the connection device 203 to pair with the physically closest device with a discoverable NFC transceiver. As the operator tapped the connection device 203 against the peripheral device 202 to run the Tap-to-Associate Subroutine, the devices 202, 203 are physically closest to one another as well. As a result, the connection device 203 pairs with the host device 201. As a result, the NFC connection 304b pairs the connection device 203 and the peripheral device 202. The connection device 203 then can retrieve the PERIPHERAL label 319b and the identifier 317b of the peripheral device 202 using the NFC connection 304b. The connection device 203 also can send the CONNECTOR label 319c and the identifier 317c to the peripheral device 202 using the NFC connection 304b.

After the second iteration of the Pairing Subroutine is complete, the connection device 203 can initiate the Association Subroutine 314 to determine the nodes connected by the wireless association and the type of wireless association formed. As the label 319c of the connection device 203 is CONNECTOR, the Association Subroutine 314 can identify the identifiers 317a, 317b stored on the connection device 203 as the nodes of the wireless association 310. The identifier 317b is associated with the PERIPHERAL label 319b, and the identifier 317a is associated with the HOST label 319a. As a result, the Association Subroutine 314 can set the peripheral device 202 to be an input device for the host device 201. In other words, the Association Subroutine 314 can form the wireless association 310 such that the host device 201 grants input permissions to the peripheral device 202.

Still referring to FIG. 3B, while the connection device 203 has been described above to implement the Association Subroutine 314 to form the wireless association 310 between the host device 201 and the peripheral device 202, in some implementations, the host device 201 can implement the Association Subroutine 314. For example, using NFC connections, the connection device 203 can retrieve the connection information of the peripheral device 202 using the Pairing Subroutine. Without proceeding to the Association Subroutine 314, the connection device 203 uses the Pairing Subroutine again. During the second iteration of the Pairing Subroutine, the connection device 203 delivers the connection information of the peripheral device 202 to the host device 201 so that the host device 201 can initiate the Association Subroutine 314 to form the wireless association between the host device 201 and the peripheral device 202. As a result, the connection device 203 does not perform the subroutine to establish the wireless association but rather delivers information such that the host device 201 can establish the wireless association. In other implementations, a server of the wireless network can implement the Association Subroutine.

Figure 4A:
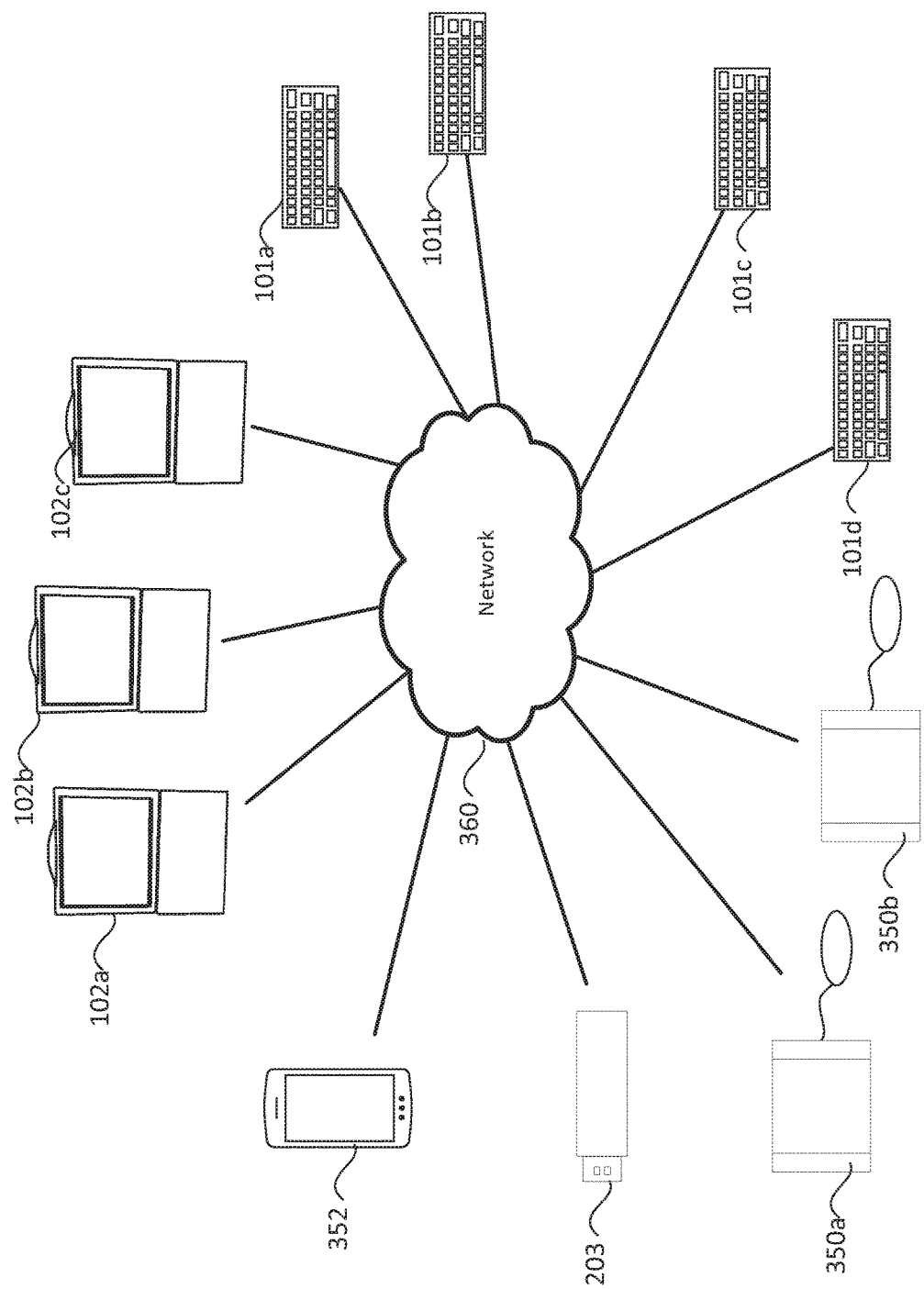
FIG. 4A is a network of hemodialysis systems and accessories in a clinic.
Figure 4C:
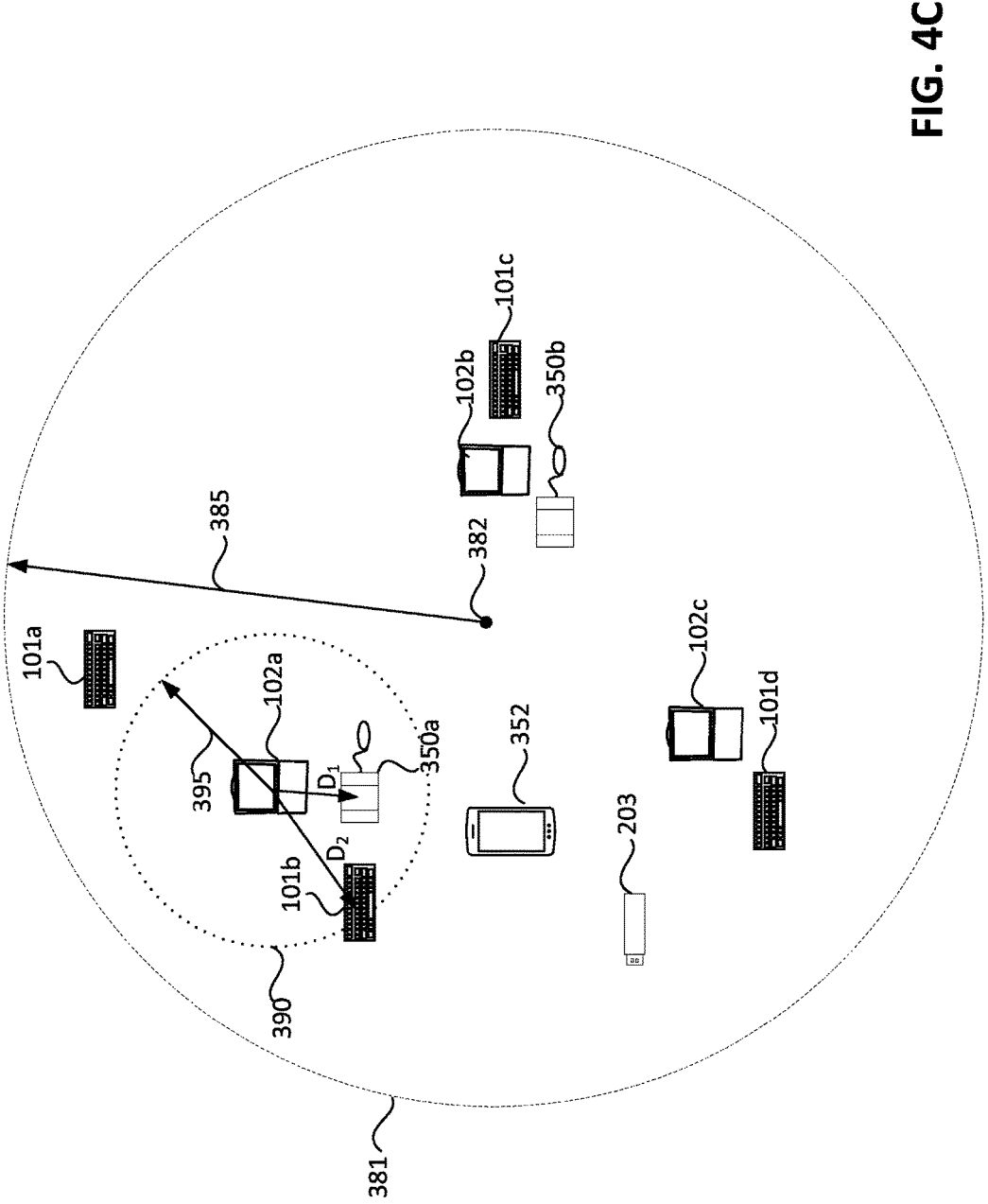
FIG. 4C is a schematic diagram of the network of FIGS. 4A-B with devices and accessories at various locations within the clinic.

FIGS. 4A-C depict an example network of hemodialysis machines and accessory devices situated, e.g., in a clinic. The network contains several connected machines and accessories at various physical locations throughout the clinic. FIG. 4A schematically depicts the wireless network 360 connecting the hemodialysis machines and accessory devices. FIG. 4B schematically depicts the wireless associations and NFC connections between the devices. FIG. 4C schematically represents the physical locations of the devices throughout the clinic.

Referring to FIG. 4A, various devices including hemodialysis machines 102a-c, a smartphone 352, the connection device 203, keyboards 101a-d, and blood pressure cuffs 350a-b are connected to the wireless network 360. Each connected device has an identifier (e.g., a unique Internet Protocol address) that distinguishes the device on the wireless network 360 from other devices. Each connected device further has a label (e.g., HOST, PERIPHERAL, CONNECTOR) that reflects its use in the clinic. The hemodialysis machines 102a-c have HOST labels, the connection device 203 have CONNECTOR label, and the keyboards 101a-d and the blood pressure cuffs 350a-b have PERIPHERAL labels. The smartphone 352 may be labeled as either PERIPHERAL or CONNECTOR. For example, in some cases, the smartphone 352 can be used as an input device similar to the keyboards 101a-d and thus has a PERIPHERAL label. In other cases, the smartphone 352 can be used as a connection device similar to the connection device 203 and thus has a CONNECTOR label. In the example represented in FIGS. 4A-C, the smartphone 352 has a PERIPHERAL label. The devices have basic wireless connections with one another. The devices can thus determine the identifiers and the labels of each other device connected to the wireless network 360.

FIG. 4B shows a node diagram of the connections between the devices of FIG. 4A. FIG. 4B shows wireless associations 365a-i in the network, which are represented by dashed lines, and NFC connections 370a-b, which are represented by solid lines. The wireless associations 365a-i represent associations over the wireless network 360 of FIG. 4A. These associations or connections have been formed using the NFC-facilitated Tap-to-Associate methods described above with respect to FIGS. 2-3.

The hemodialysis machine 102a has formed respective wireless associations 365a-c with the smartphone 352, the blood pressure cuff 350a, and the keyboard 101a. As the hemodialysis machine 102a has a HOST label, the smartphone 352, the cuff 350a, and the keyboard 101a serve as input devices for the hemodialysis machine 102a. The blood pressure cuff 350a, which an operator can use to detect the blood pressure of a patient, delivers blood pressure measurements to the hemodialysis machine 102a. The hemodialysis machine 102a can display the blood pressure measurements to the operator (e.g., on the touch screen 118) or can activate an alarm if the blood pressure measurements decreases or increases beyond a threshold blood pressure. As described above, the operator can change treatment parameters of the hemodialysis machine 102a using touch screen 118 and the control panel 120. The operator can also use the keyboard 101a to control the treatment parameters of the hemodialysis machine 102a. For example, the operator types numbers into the keyboard 101a, and the touch screen of the hemodialysis 102a will display the input from the keyboard 101a. The operator can change parameters such as flow rate or issue stop and start commands using the keyboard 101a. The hemodialysis machine 102 has also granted input permissions to the smartphone 352 such that the operator can use the smartphone 352 to issue commands to the hemodialysis machine 102a.

The blood pressure cuff 350a is further connected to the keyboard 101b using the wireless association 365d. As the blood pressure cuff 350a and the keyboard 101b are both PERIPHERAL devices, the operator selects which device serves as the input device for the other device (e.g., using a connection device as described above). In this example, the operator has chosen the keyboard 101b to serve as an input device for the blood pressure cuff 350a. As a result, the keyboard 101b controls operations of the blood pressure cuff 350a. The operator can use the keyboard 101b to start or stop the blood pressure cuff 350a or instruct the blood pressure cuff to perform other functions (e.g., send data to another device, sense pressure periodically every 10 minutes, etc.).

The smartphone 352 has the wireless association 365e with the hemodialysis machine 102b in addition to the wireless association 365a with the hemodialysis machine 102a. As a result, the smartphone 352 can serve as an input device for both machines 102a-b. The operator can use the smartphone 352 to control both machines 102a-b simultaneously. For example, in a case where both machine 102a-b need to be stopped simultaneously (due to, e.g., an earthquake or an attack or another emergency situation), the operator can stop both machines using the smartphone 352 associated with both machines 102a-b. The smartphone 352 can also be used to control each machine 102a-b individually. The operator can toggle between using the user interface (e.g., a touch screen of the smartphone) to control the hemodialysis machine 102a and using the user interface, which can include the touch screen 118 and the control panel 120 of the hemodialysis machine 102a, to control the hemodialysis machine 102b. A user application can be loaded onto the smartphone 352 to facilitate the functions described above.

The hemodialysis machine 102b also has the wireless association 365f with the blood pressure cuff 350b (with a similar function as the wireless association 365b between the blood pressure cuff 350a and the hemodialysis machine 102a) and the wireless association 365g with the keyboard 101c. The keyboard 101c has two wireless associations: the wireless association 365g and the wireless association 365h. The keyboard 101c serves as an input device for both the hemodialysis machine 102b and the blood pressure cuff 350b. The operator can, in some examples, switch between delivering commands to the hemodialysis machine 102b and the blood pressure cuff 350b by pressing a switch key on the keyboard 101b.

The wireless association 365i connects the hemodialysis machine 102c to the keyboard 101d, which serves as an input device for the hemodialysis machine 102c. The hemodialysis machine 102c has further formed the NFC connection 370b with the connection device 203. The connection device 203 can be used to form two NFC connections: the NFC connection 370a with the smartphone 352 and the NFC connection 370b with the hemodialysis machine 102c. As a result, the connection device 203 has the identifiers and labels for the smartphone 352 and the hemodialysis machine 102. The connection device 203 can be prepared to form a wireless association between the smartphone 352 and the hemodialysis machine 102c so that the smartphone 352 can have a wireless association with all of the hemodialysis machines 102a-c located in the example clinic.

FIG. 4C schematically represents the physical locations of the devices in the clinic described in FIGS. 4A-B. A wireless router 382 creates the wireless network 360 of FIG. 4A, which has a wireless coverage region 381. The wireless coverage region 381 is represented by a circle centered at the position of the wireless router 382 with a radius of a wireless range 385. Devices within the wireless coverage region 381 can form basic wireless connections with other devices within the wireless range 381.

Each device has an NFC transceiver and therefore forms an NFC coverage region. In FIG. 4C, the NFC coverage region 390 around the hemodialysis machine 102a is shown, though it should be understood that the remaining devices also form NFC coverage regions. The NFC coverage region 390 is defined by a circle centered at the position of the hemodialysis machine 102a with a radius of an NFC range 395. Devices within the NFC coverage region 390 generally can detect a strong enough signal from the NFC transmitter of the hemodialysis machine 102a to form an NFC connection with the hemodialysis machine 102a. As shown in FIG. 4C, the keyboard 101a is outside of the NFC coverage region 390. Referring briefly back to FIG. 4B, the keyboard 101a has formed the wireless association 365c with the hemodialysis machine 102a, so, even though the keyboard 101a is outside of the NFC coverage region 390, the keyboard 101a can still be used to control the hemodialysis machine 102a. Once the wireless association 365c is formed, the operator can move the keyboard 101a outside of the NFC coverage region 390 of the hemodialysis machine 102a and the wireless association 365c will remain intact as both the hemodialysis machine 102a and the keyboard 101a are still both within the wireless coverage region 381.

The blood pressure cuff 350a and the keyboard 101b are both within the NFC coverage region 390 and therefore both can form an NFC connection with the blood hemodialysis machine 102a. The blood pressure cuff 350a is located a distance $D_1$ from the hemodialysis machine 102a, and the keyboard 101b is located a distance $D_2$ from the keyboard 101b. The NFC signal strength decreases proportional to the inverse square of the distance from the source. As the distance $D_2$ is greater than the distance $D_1$, the NFC signal from the blood pressure cuff 350a is stronger than the NFC signal from the keyboard 101b. The hemodialysis machine 102a can thus determine that the blood pressure cuff 350a is closer than the keyboard 101b. As a result, if the operator triggers the Tap-to-Associate Subroutines of the blood pressure cuff 350a and the hemodialysis machine 102a, the blood pressure cuff 350a can form a wireless association (e.g., the wireless association 365b of FIG. 4B) with the hemodialysis machine 102a.

Generally, an operator establishes the connection between the first and the second medical devices such that the operator can use the second medical device to, for example, control operations or provide data to the first medical device. The first medical device can be, for example, a hemodialysis machine. The second medical device can be, for example, a wireless keyboard. The first medical device, the second medical device, and the connection device are equipped with first transceivers to connect to a first network that connects medical devices to one another using a first communication protocol (e.g., NFC). The first medical device, the second medical device, and the connection device are further equipped with second transceivers that connect to a second network that connects medical devices to one another using a second communication protocol (e.g., WPA, WPA2, WEP, etc.).

Figure 5:
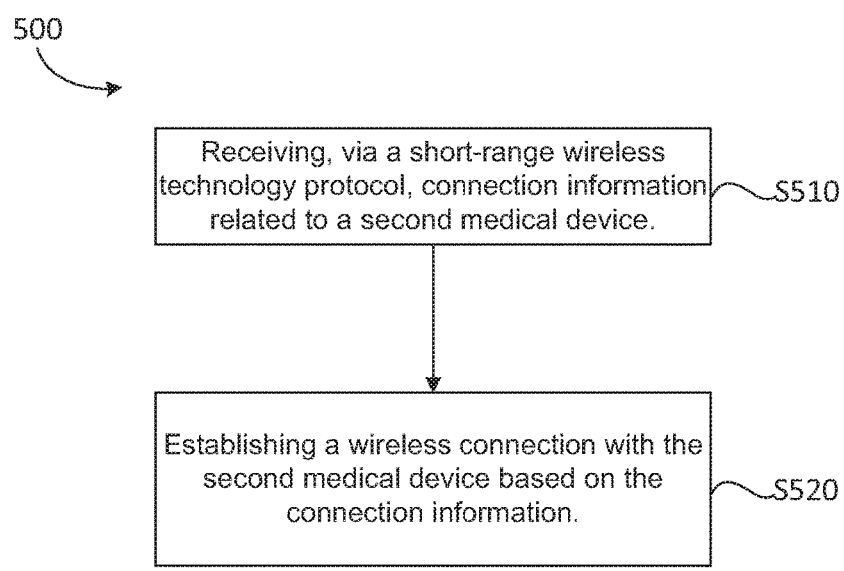
FIG. 5 is a flowchart depicting an example of a process for connecting a first medical device to a second medical device.

FIG. 5 is a flowchart 500 of establishing a wireless connection between a first medical device and a second medical. At step S510, via a short-range wireless technology protocol, connection information related to the second medical device is received. The connection information can be received by the first medical device. In some examples, the short-range wireless technology protocol is an NFC protocol. In some examples, the first medical device is a hemodialysis machine, and the second medical device is a wireless keyboard configured to interact with the hemodialysis machine. In some examples, the first medical device first receives, via the short-range wireless technology protocol, a request to establish a wireless connection using a communication protocol other than the short-range wireless technology protocol. The wireless connection can be between the first medical device and the second medical device. The connection information can specify information used by the communication protocol other than the short-range wireless technology protocol. Prior to receiving the request, the first medical device can be placed in a discoverable state such that the second medical device detects the first medical device using the short-range wireless technology protocol. The second medical device can also be placed in a discoverable state such that the first medical device detects the second medical device using the short-range wireless technology protocol. The first and second medical devices can contain the subroutines as described above with respect to FIG. 2B. As a result, the first and second medical devices can be placed in discoverable states by triggering the Tap-to-Associate Subroutines. Upon triggering the Tap-to-Associate Subroutines, the second medical device can also send the request to establish the wireless connection to the first medical device. One or both medical devices can be mobile such that the operator can move one or both medical devices within communication range using the first communication protocol. The operator can instruct the first medical device to accept the request, and then the first medical device receives the connection information related to the second medical device using the short-range wireless technology protocol. The first medical device can also send, via the short-range wireless technology protocol, connection information related to the first medical device to the second medical device. The connection information for each device can include an identifier and a label of the device. The transfer of connection information between the first and second medical devices can occur as part of the Pairing Subroutine described with respect to FIG. 2B.

At step S520, the wireless connection is established between the first medical device and the second medical device. In some examples, the first medical devices establishes the wireless connection. Referring back to the Association Subroutine described with respect to FIG. 2B, the first medical device can use the unique identifier of the first medical device and the unique identifier of the second medical device as the nodes of the wireless network. The labels of the first and second medical devices can determine the type of wireless connection established between the first and second medical devices. From the above steps, it should be understood the connection information associated with the communication protocol can be transmitted via the short-range wireless technology protocol. The connection information can then be used to establish the permanent wireless connection using the communication protocol.

Figure 6A:
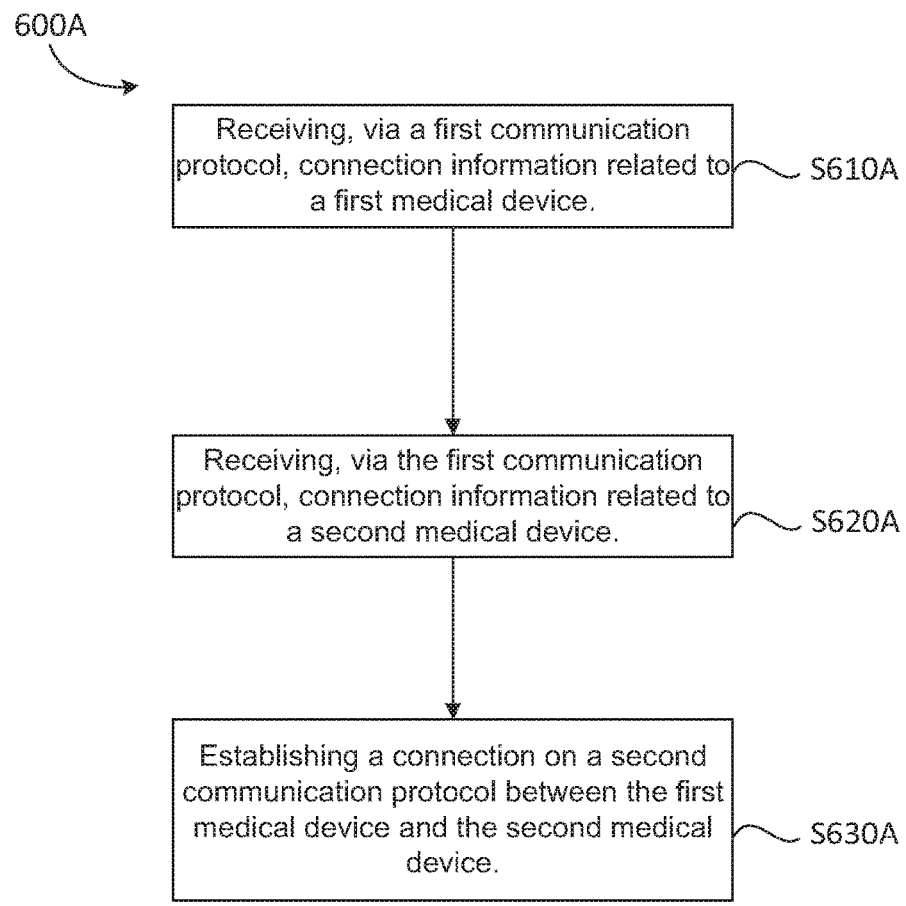
FIGS. 6A-B are flowcharts depicting examples of processes for connecting a first medical device to a second medical device using a connection device.
Figure 6B:
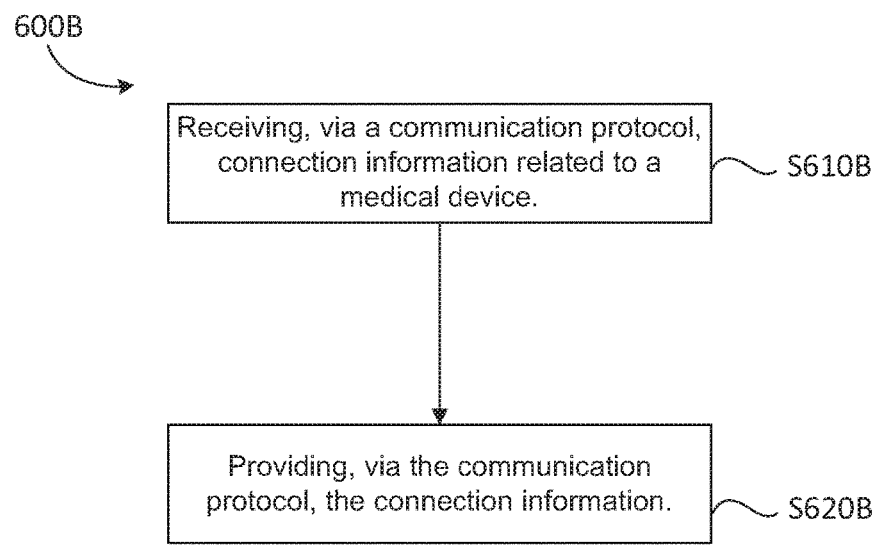

FIGS. 6A-6B are flowcharts 600A-B of establishing a connection, such as the wireless associations described above, between a first medical device and a second medical using a connection device. In the flowchart 600A of FIG. 6A, a connection device establishes the wireless connection between the first and second medical device.

At step S610A, the connection device receives, via a first communication protocol, connection information related to a first medical device. In some examples, the first communication protocol is an NFC protocol. In some examples, the first medical device is a hemodialysis machine, the second medical device is a wireless keyboard configured to interact with the hemodialysis machine, and the connection device is a smartphone or a wand.

At step S620A, the connection device receives, via the first communication protocol, connection information related to a second medical device. The operator can trigger the Tap-to-Associate Subroutine on the connection device with each of the first and second medical devices. As a result, the connection device can execute the Pairing Subroutine and can receive connection information from both the first medical device and the second medical device.

At step S630A, the connection device establishes a connection on a second communication protocol between the first medical device and the second medical device. The connection device implements the Association Subroutine, which uses the connection information received in steps S610A and S620A to establish the connection between the first and second medical devices and determine the type of connection formed between the first and second medical devices. In some examples, the second communication protocol is a wireless protocol such as WEP, WPA, or WPA2.

The flowchart 600B of FIG. 6B depicts an alternative implementation of establishing a wireless connection between the first and second medical device using the connection device. A connection device provides connection information of the first medical device to establish a wireless connection between, for example, the first medical device and the second medical device.

At step S610B, the connection device receives, via a communication protocol, connection information related to the first medical device. The connection device can execute a first iteration of the Pairing Subroutine and receives connection information from the medical device.

At step S620B, the connection device provides, via the communication protocol, the connection information. The connection device can provide the connection information to the second medical device to establish the wireless connection. The connection device can also provide the connection information to a server of a wireless network through which the wireless connection is formed. The connection device can execute a second iteration of the Pairing Subroutine and sends the previously received connection information to the second medical device. The second medical device can then implement the Association Subroutine to establish the wireless connection between the first medical device and the second medical device.

Figure 7:
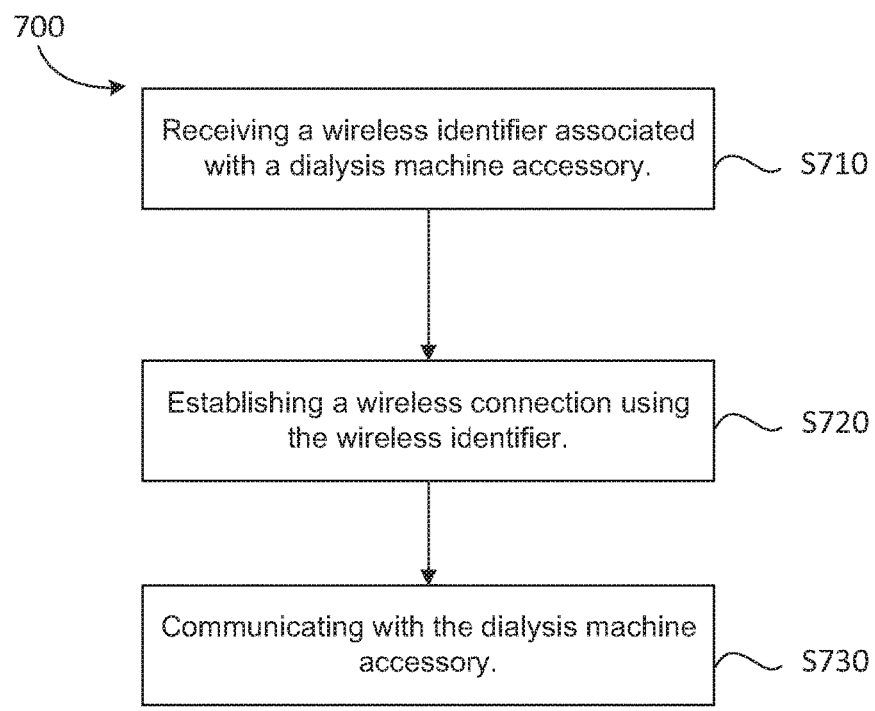
FIG. 7 is a flowchart depicting an example of establishing a wireless connection between a dialysis machine and a dialysis machine accessory.

FIG. 7 is a flowchart 700 of establishing a wireless connection between a dialysis machine and a dialysis machine accessory.

At step S710, a wireless identifier associated with the dialysis machine accessory is received. In some examples, the dialysis machine receives the wireless identifier. The wireless identifier can be communicated by a connection device according to a first wireless communication protocol. The wireless identifier can be associated with a second wireless communication protocol other than the first wireless communication protocol. In some examples, the first wireless communication protocol is an NFC protocol and the second wireless communication protocol is WPA, WPA2, or WEP.

At step S720, a wireless connection is established using the wireless identifier associated with the dialysis machine accessory. In some examples, the dialysis machine establishes the wireless connection. In other examples, the dialysis machine accessory establishes the wireless connection. The wireless connection can be established using the second wireless communication protocol.

At step S730, the dialysis machine accessory can be communicated with. In some examples, the dialysis machine communicates with the dialysis machine accessory; in some examples, the dialysis machine accessory communicates with the dialysis machine; and in other examples, two-way communication occurs between the dialysis machine and the dialysis machine accessory. Medical data can be communicated between the dialysis machine and the dialysis machine accessory using, for example, the wireless connection.

While certain implementations have been described, other implementations are possible.

In the block diagram of FIG. 2A depicting an example communications system 201 of a device 200, the communications system 201 is described to include a wireless transceiver 303, an NFC transceiver 305, a user interface 308, a memory storage element 309, and a sensor system 315. In alternative implementations, the device does not include one or more of a wireless transceiver, an NFC transceiver, a user interface, a memory storage element, and a sensor system. For example, in some implementations, the device does not have a user interface but can still be used with the subroutines and methods described in this application. In other examples, the device does not have both a wireless transceiver and an NFC transceiver. The device can include just a wireless transceiver and use the wireless transceiver to pair with other devices and to form a wireless association with other devices. The sensor system is an optional system within the communications system.

While FIG. 2A depicts the device 200 to have an identifier and a label, in some implementations, the device can have only an identifier. In such implementations, when an association been formed between two devices, an operator can indicate on a user interface of either device which device serves as a host device and which serves as a peripheral device.

While the communication systems 201 of the device 200 of FIG. 2A has been described as a generic communications system for devices herein (e.g., a hemodialysis machine, a keyboard, a connection device, a blood pressure cuff, etc.), in some implementations, the communications system of a device only includes a subset of the sub-systems and hardware described. Some devices may only include a subset of the subroutines described. For instance, in some implementations, only devices with the HOST label have the Association Subroutine. As a result, connection information is delivered only to the devices with HOST labels, and the host devices accordingly form the wireless associations between devices. Connection devices and peripheral devices assist in delivering information to the host devices.

While the label 319 of the device 200 has been described to be one of HOST, PERIPHERAL, or CONNECTOR, in some implementations, additional labels can be used to further classify a device. For example, the PERIPHERAL label can include sub-labels, such as INPUT, OUTPUT, or SENSOR, that represent the specific function of the PERIPHERAL device.

While the peripheral device 202 has been described to serve as an input device for the host device 201, in other implementations, the peripheral device serve other functions as well. For example, the peripheral device can be an external speaker that amplifies alarms and alerts triggered by the hemodialysis machine. The peripheral device is an output device in such an example. The peripheral device can also be a treatment accessory, such as a drug vial or salt solution container. For example, the salt solution container can be a flexible bag with a sensor that monitors conductivity of the salt solution within the container. The container can be paired with the hemodialysis machine such that the container wireless transmits conductivity sensor data to the hemodialysis machine. Peripheral devices can include remote controllers, laptops, desktops, stethoscopes, thermometers, and saline containers, among other dialysis treatment-related peripheral devices.

Referring to the Tap-to-Associate Subroutine described with respect to FIG. 2B, when the operator taps a first device against a second device, the Tap-to-Associate Subroutines of both devices can be triggered causing a request to pair to be sent to both devices. In some implementations, to initiate the pairing, the request is accepted on both devices. In other implementations, to initiate the pairing, the request is accepted on at least one of the devices.

Referring to the Pairing Subroutine 313 of FIG. 2B, the operator has been described to manually accept the request sent by the device 200 using the second device. In other implementations, the operator can modify default Pairing Subroutine settings to a manual mode or an automatic mode. In a manual mode, the operator manually operates the second device to accept the request to pair the devices together, as described above. In an automatic mode, the second device can automatically accept the request to form the NFC connection such that the operator just operates the device 200 to form the NFC connection. The request has also been described as a request to establish an NFC connection between a first device and a second device. The request can also represent a request to initiate the process of establishing the wireless association. Thus, accepting the request grants permission to both devices to form the NFC connection, to transmit wireless connection information to one another, and to establish the wireless association.

While information transmitted and stored using the Pairing Subroutine has been described to be the same regardless of the device label, in some implementations, if one of the devices involved in the Pairing Subroutine has a CONNECTOR label, only the device with the CONNECTOR label stores the connection or identity information of the device to which it is paired. The device that does not have the CONNECTOR label does not use the connection information, so such implementations reduces the amount of unused data stored on the device.

While triggering the Tap-to-Associate Subroutine has been described to initiate the Discover Subroutine and the Pairing Subroutine, in some implementations, the Tap-to-Associate subroutine only initiates the Pairing Subroutine. The operators may manually initiate the Discover Subroutine prior to triggering the Tap-to-Associate Subroutine. In some implementations, the subroutines may not include a Tap-to-Associate Subroutine. The operator can trigger the Discover and the Pairing Subroutines manually using, for example, a user interface on the device. Alternatively, the Discover Subroutine is, by default, automatically executing and can cause the device to search for nearby devices with which to pair. In such implementations, the device can be constantly scanning for nearby devices with enabled NFC transceivers.

Referring to the Pairing Subroutine, while the operator has been described to accept the request to pair on one device, in some implementations, the request to pair is accepted on both devices in order to initiate the pairing subroutine.

Referring back to FIGS. 3A-B, in some implementations, pairings may not automatically occur between devices as part of the Pairing Subroutine. Rather, a request to pair is first sent prior to establishing the pairing. For example, referring to FIG. 3A, the Pairing Subroutine can cause the peripheral device 202 to send a request to pair with the host device 201. The operator may need to instruct the host device 201 to accept a pairing request from the peripheral device 202, prompting the NFC connection 304 to be established between the peripheral device 202 and the host device 201. The operator can instruct the host device 201 to accept the request using, for example, a user interface on the host device 201 or the peripheral device 202.

Referring to the example of FIG. 3B, while the connection device 203 has been described to determine the type of wireless association 310 to form between the keyboard 101 and the hemodialysis machine 102 based on the labels 319*a*, 319*c*, in some implementations, the connection device receives permission from the keyboard and the hemodialysis machine to deliver identifiers and labels to each device. The keyboard and/or the hemodialysis machine then requests the devices linked to the identifiers and determines the type of wireless association based on the labels. For example, in some cases, the connection device may not have a wireless transceiver. As a result, to initiate a wireless association between a first device and a second device, the connection device receives an identifier from a first device and then delivers the identifier to a second device. The second device then requests to form a wireless association with the device associated with the identifier (i.e. the first device).

Referring to FIG. 3B, in some implementations, the connection device can further include a Universal Serial Bus (USB) connector so that the connection device 203 can connect with a device through a USB port.

While the Tap-to-Associate Subroutine has been described to use the acceleration sensed by the sensor system to determine whether a tap motion has occurred, in some implementations, other sensors of the sensor system can be used that allows an operator to physically trigger the subroutines. For example, the sensors can be replaced by pushbuttons that the operator actuates when the operator associates two devices. The sensor can also be replaced by pressure sensors, strain sensors, or other sensors that react to physical phenomena that the operator can easily generate manually. In some implementations, the sensor system includes a high-frequency radiofrequency identification (RFID) tag and a corresponding RFID detector. When two devices with the RFID tag and detector come in close proximity to another, the Tap-to-Associate Subroutine is triggered. While the Tap-to-Associate Subroutine has been described to be automatically executing, the operator can set the default settings such that the operator manually initializes the Tap-to-Associate Subroutine of a device. As a result, the operator can, for example, move the device around the room without inadvertently triggering the Tap-to-Associate Subroutine. In some examples, a first device triggers the Tap-to-Associate Subroutine by making physical contact with a second device.

While the NFC connection 304 are shown as intact in FIG. 3A and the NFC connections 304*a-b* are shown as intact in FIG. 3B, in some implementations, the devices can sever the NFC connections after forming the wireless association between the host device and the peripheral device. In other implementations, the connection device maintains the NFC connection until a user instructs the connection device to break the connection.

While the connection device 203 has been described to establish a connection between two devices, in some implementations, it should be understood that the connection device can be used to establish connections with more than two devices. For example, the connection device can connect with three devices and establish connections between all of the three devices. The connection device 203 can be used to create wireless associations between more than two devices. For example, the operator can trigger the Tap-to-Associate Subroutine of the connection device 203 with three or more other devices having HOST or PERIPHERAL labels. The connection device 203 thus receives connection information from the three or more devices. The operator can then instruct the connection device 203 to form wireless associations between the three or more devices. Based on the labels, the Association Subroutine can automatically select the permission granted over the wireless associations. In other implementations, the operator can use the user interface of the connection device 203 to manually select the permissions granted by each wireless association.

Referring to FIG. 4A, while the identifiers have been described as IP addresses, in some implementations, the identifiers can be device names, serial numbers, or other identifying information that can be determined through the wireless network. Referring to FIGS. 4A-C, while a HOST device such as the hemodialysis machines 102*a-c* have been described to have wireless associations with one, two, or three PERIPHERAL devices, it should be understood that a HOST device can accept wireless associations with more than three PERIPHERAL devices. In addition, a PERIPHERAL device can have wireless associations with two or more devices. For example, a first PERIPHERAL device can serve as input devices for two HOST devices. The first PERIPHERAL device can serve as input devices for two additional PERIPHERAL devices. A second PERIPHERAL device can serve as an input device for the first PERIPHERAL device.

Referring back to FIG. 4B, the blood pressure cuff 350a has been described as connected to the keyboard 101b. In some implementations, PERIPHERAL devices, such as the blood pressure cuff and the keyboard, can have a priority rank. In the cases where a wireless association is formed between two PERIPHERAL devices, the device with the higher priority rank grants permission to the other device so that the other device can serve as an input. In cases where the two PERIPHERAL devices have the same priority rank, the user can indicate instructions to the devices over a user interface on one of the devices or on the user interface of another device, such as a smart phone.

A number of embodiments of the invention have been described. Nevertheless, it will be understood that various modifications may be made without departing from the spirit and scope of the invention. Accordingly, other embodiments are within the scope of the following claims.

While only one controller is described, multiple controllers may alternatively be used.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a display device (e.g., the display device of the dialysis machine 12), for example, a CRT (cathode ray tube) or LCD (liquid crystal display) monitor, for displaying information to the user and a keyboard or keypad and/or a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

Other implementations are within the scope of the following claims.

What is claimed is:

1. A system comprising:
   a mobile device;
   a dialysis machine comprising:
      a first antenna configured to receive a wireless identifier related to the mobile device via a short-range wireless technology protocol; and
      a second antenna configured to communicate with the mobile device via a communication protocol other than the short-range wireless technology protocol; and
   a server configured to communicate with one or both of the mobile device or the dialysis machine, the server configured to cause a wireless connection to be established between the mobile device and the dialysis machine, using the wireless identifier, to allow the mobile device and the dialysis machine to communicate with each other via the communication protocol;
   wherein the mobile device is granted permission to deliver data to the dialysis machine using the wireless connection.

2. The system of claim 1, wherein the first antenna receives the wireless identifier from the mobile device as a result of detecting that the dialysis machine and the mobile device are positioned within a communication range of the short-range wireless technology protocol.

3. The system of claim 1, wherein the first antenna receives the wireless identifier from the mobile device as a result of the dialysis machine and the mobile device making physical contact with each other, and one or both of the dialysis machine and the mobile device includes an accelerometer configured to detect the physical contact.

4. The system of claim 1, comprising a connection device, wherein the connection device is configured to:
   receive, from the mobile device, via the short-range wireless technology protocol, the wireless identifier; and
   provide, to the first antenna, via the short-range wireless technology protocol, the wireless identifier.

5. The system of claim 4, wherein the connection device is a wand or a smartphone.

6. The system of claim 4, wherein the connection device is configured to provide the wireless identifier to the server.

7. The system of claim 1, wherein the mobile device is configured to receive, via the short-range wireless technology protocol, connection information related to the dialysis machine.

8. The system of claim 1, wherein the short-range wireless technology protocol is a Near Field Communication (NFC) protocol or a Bluetooth protocol.

9. The system of claim 1, wherein the wireless identifier is unique to the mobile device.

10. A method comprising:
    establishing a wireless connection between a mobile device and a dialysis machine, the method comprising:
       receiving, by the dialysis machine, via a short-range wireless technology protocol, a wireless identifier related to the mobile device;
       communicating, by the dialysis machine, via a communication protocol other than the short-range wireless technology protocol, with the mobile device; and
       establishing, by the dialysis machine, a wireless connection with the mobile device using the wireless identifier, the wireless connection for allowing the mobile device and the dialysis machine to communicate with each other via the communication protocol, wherein a server is configured to communicate with one or both of the mobile device or the dialysis machine and cause the wireless connection to be established;
    wherein the mobile device is granted permission to deliver data to the dialysis machine using the wireless connection.

11. The method of claim 10, wherein the wireless identifier is received from the mobile device as a result of detecting that the dialysis machine and the mobile device are positioned within a communication range of the short-range wireless technology protocol.

12. The method of claim 10, wherein the wireless identifier is received from the mobile device as a result of the dialysis machine and the mobile device making physical contact with each other, and one or both of the dialysis machine and the mobile device includes an accelerometer configured to detect the physical contact.

13. The method of claim 10, wherein a connection device is configured to:
    receive, from the mobile device, via the short-range wireless technology protocol, the wireless identifier; and
    provide, to the dialysis machine, via the short-range wireless technology protocol, the wireless identifier.

14. The method of claim 13, wherein the connection device is a wand or a smartphone.

15. The method of claim 13, wherein the connection device is configured to provide the wireless identifier to the server.

16. The method of claim 10, wherein the mobile device is configured to receive, via the short-range wireless technology protocol, connection information related to the dialysis machine.

17. The method of claim 10, wherein the short-range wireless technology protocol is a Near Field Communication (NFC) protocol or a Bluetooth protocol.

18. The method of claim 10, wherein the wireless identifier is unique to the mobile device.

* * * * *